United States Patent
De Boer et al.

(10) Patent No.: US 6,574,305 B2
(45) Date of Patent: Jun. 3, 2003

(54) DEVICE AND METHOD FOR THE INSPECTION OF THE CONDITION OF A SAMPLE

(75) Inventors: Dirk Kornelis Gerhardus De Boer, Eindhoven (NL); Evert Jan Van Loenen, Eindhoven (NL)

(73) Assignee: Koninklijke Philips Electronics, N.V., Eindhoven (NL)

( * ) Notice: Subject to any disclaimer, the term of this patent is extended or adjusted under 35 U.S.C. 154(b) by 0 days.

(21) Appl. No.: 09/988,844

(22) Filed: Nov. 19, 2001

(65) Prior Publication Data

US 2002/0085669 A1 Jul. 4, 2002

(30) Foreign Application Priority Data

Nov. 20, 2000 (EP) .............................. 00204104

(51) Int. Cl.⁷ ............................................ G01N 23/207
(52) U.S. Cl. ............................................ 378/83; 378/82
(58) Field of Search ........................ 378/81, 82, 83, 378/84, 85, 86, 71

(56) References Cited

U.S. PATENT DOCUMENTS

| | | | | | |
|---|---|---|---|---|---|
| 4,562,585 A | * | 12/1985 | Gobel et al. | .................. | 378/83 |
| 4,800,580 A | * | 1/1989 | Houtman et al. | ............. | 378/83 |
| 4,910,758 A | * | 3/1990 | Herrick | ........................ | 378/83 |
| 5,115,460 A | * | 5/1992 | De Lange | ....................... | 378/81 |
| 5,414,747 A | * | 5/1995 | Ruud et al. | .................... | 378/83 |
| 5,459,770 A | * | 10/1995 | Salje | ............................ | 378/81 |
| 5,619,548 A | * | 4/1997 | Koppel | ......................... | 378/84 |
| 6,453,006 B1 | * | 9/2002 | Koppel et al. | ................. | 378/86 |

FOREIGN PATENT DOCUMENTS

DE          4137673          5/1993         G07N/21/55

* cited by examiner

*Primary Examiner*—Drew A. Dunn
(74) *Attorney, Agent, or Firm*—Aaron Waxlef

(57) ABSTRACT

A device and method having a stationary radiation source for directing polychromatic radiation such that the radiation is incident on a sample to be inspected in parallel or diverging rays, and a position-sensitive, energy-sensitive detector for measuring components of the radiation reflected by the sample thereby providing for the efficient and effective inspection of the sample.

15 Claims, 1 Drawing Sheet

DEVICE AND METHOD FOR THE INSPECTION OF THE CONDITION OF A SAMPLE

BACKGROUND OF THE INVENTION

1. Field of the Invention

The present invention relates to a device and method for the inspection of the condition of a sample. In particular, the present invention relates to a device and method utilizing a simple arrangement of a stationary radiation source for directing polychromatic radiation such that the radiation is incident on the sample in parallel or diverging rays, and a position-sensitive, energy-sensitive detector for measuring components of the reflected radiation to efficiently and effectively inspect the sample.

2. Description of the Related Art

A method of this kind and corresponding devices are known, for example, from DE 41 37 673 A1 which discloses a reflectometer whereby radiation that is bundled on and reflected from a point of a sample to be inspected is measured simultaneously in different zones a position-sensitive detector; information concerning the density, roughness and thickness of a surface layer of the sample can then be derived therefrom. Therein, the angle of incidence of the radiation is chosen so as to be fixed, that is, near the critical angle for total reflection. In comparison with known goniometers, the device offers the advantage that the angle of incidence of the radiation source need not be varied during the measurement and that hence the position of the detector need not be adapted either. It is a drawback of such a reflectometer, however, that each time only a very small, almost punctiform area of the sample can be inspected. In order to derive information concerning a larger area of the sample, therefore, it is necessary to perform a time-consuming plurality of measurements. The focusing of the radiation, moreover, imposes the risk of modification or damaging of the surface of the sample.

BRIEF SUMMARY OF THE INVENTION

Therefore, the invention thus has for its object to modify a device of the kind set forth above and a corresponding method such that a larger area of the sample can be inspected within a short period of time This object is achieved in accordance with the invention by means of a device and a method having a stationary radiation source for directing polychromatic radiation such that the radiation is incident on the sample in parallel or diverging rays, and a position-sensitive, energy-sensitive detector for measuring components of the reflected radiation.

Because the radiation source is constructed and oriented in such a manner that the radiation is incident on the sample in parallel or diverging rays, a larger area of the sample can be irradiated at the same time; the rays are reflected from said larger area and reach different zones of the detector, each detector zone or each measuring cell of the detector corresponding to a given area on the surface of the sample. When the detector is constructed so as to be energy-sensitive in addition to position-sensitive, an energy-dependent spectrum can be measured in each detector zone or in each detector measuring cell, said spectrum providing information concerning the condition of the sample in the corresponding area. When the radiation source is constructed and arranged in such a manner that it irradiates an essentially linear area on the surface of the sample, for example, by way of parallel orientation of the radiation in one direction only, the reflected radiation that is incident on the detector can be simply related to the corresponding area on the surface of the sample. It is then advantageously possible to use an essentially linear detector in which the individual detector cells are arranged linearly adjacent one another and which is oriented so as to match the linearly irradiated area on the surface of the sample. The use of polychromatic radiation enables the acquisition of information concerning the thickness and surface roughness of the sample material and the thickness of, for example, a surface layer by application of Bragg equations for the examination of the interference phenomena. X-rays having the complete wavelength spectrum are preferably used for this purpose; radiation having a partly reduced spectrum, that is, wherefrom the source peaks have been filtered out, however, can also be used.

Favorable measuring results can be obtained by means of the measuring device in accordance with the invention and the method in accordance with the invention notably when the angle of incidence of the radiation on the surface of the sample is chosen so as to be close to the critical angle for total reflection. Therefore, radiation angles of incidence of between approximately 0.3° and 1.5° are preferably used. When diverging radiation is used, in which case the individual rays are incident on individual points on the sample surface at different angles of incidence, the radiation source should be positioned or oriented in such a manner that the angles of incidence of the individual rays on the sample lie approximately in the stated range of between 0.3 and 1.5°. The use of an at least approximately punctiform radiation source enables optimum measuring results to be obtained.

An essentially linearly irradiated area on the sample can be realized, for example, by collimating in one direction the radiation that is directed onto the sample, for example, between plates that are oriented perpendicularly to the plane of the surface of the sample, so that the line-shaped irradiation area on the surface of the sample is formed in the direction of an imaginary connecting line between the radiation source and the sample. The distance between such collimating plates preferably amounts to approximately 200 $\mu$m. The radiation can then be considered to be substantially parallel between the plates while a strip of adequate width is still irradiated on the sample, thus ensuring an adequate intensity for the energy-sensitive measurement. The device in accordance with the invention offers a good and fast measurement notably when an area whose length amounts to approximately twenty times its width is simultaneously irradiated on the sample. For example, when use is made of a radiation source that has a radiation angle or maximum divergence angle of 0.02°, a strip of 40 mm length will be simultaneously irradiated by a beam that is oriented in parallel in one direction when the distance between the radiation source and the surface of the sample amounts to 100 mm.

In order to enable the undesirable effects of diffuse scattered radiation to be taken into account for the measurement, at least one further position-sensitive, energy-sensitive detector can be arranged adjacent the first detector in such a manner that this further detector is not exposed to the directly reflected radiation but only to the diffuse scattered radiation. The energy values measured by the first detector can be corrected for the scattered radiation component by subtracting therefrom the values that have been measured by said further detector. Preferably, a further detector is provided to each side of the first detector, the detectors preferably being oriented in parallel in order to ensure that the measured results can be readily evaluated. This object is also achieved in a particularly simple manner by means of a two-dimensional detector, that is, a detector having position-sensitive, energy-selective detector cells that are arranged adjacent one another in a two-dimensional array instead of in a linear one-dimensional array.

BRIEF DESCRIPTION OF THE DRAWINGS

The invention will be described in detail hereinafter with reference to the illustrative embodiments that are shown in the Figures; therein.

DETAILED DESCRIPTION OF THE INVENTION

The illustrative embodiments shown by no means limit the numerous feasible applications of the invention. A large number of other device arrangements that utilize the ideas of the invention is feasible, that is, for example, by deflecting the radiation used or, for example, by arranging a plurality of device arrangements adjacent one another; in that case radiation could be utilized from a single line-shaped radiation source.

Figure 1:
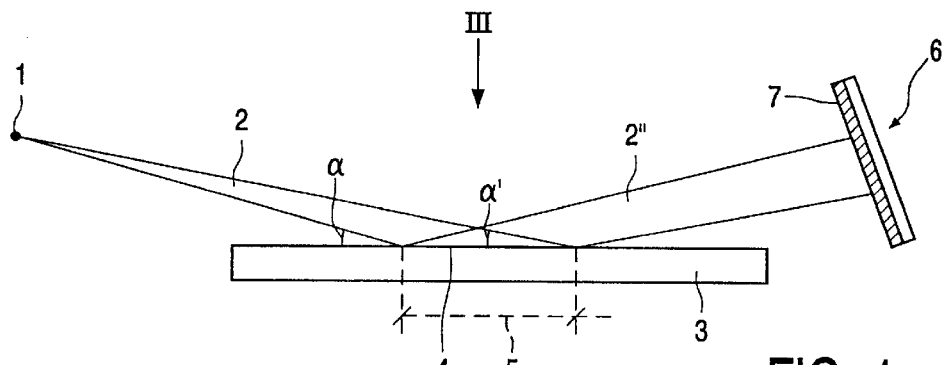
FIG. 1 is a diagrammatic side elevation of a device in accordance with the invention with diverging radiation.

FIG. 1 shows a radiation source 1 wherefrom radiation 2 is directed onto a sample 3 in diverging rays, only the two outer rays of which are shown. The rays are incident on the surface of the sample 3 on which they irradiate an area 4 of a length 5 and are reflected on the surface of the sample 3 in the direction of a position-sensitive detector 6 whose individual detector cells 7 are energy-sensitive.

Figure 2:
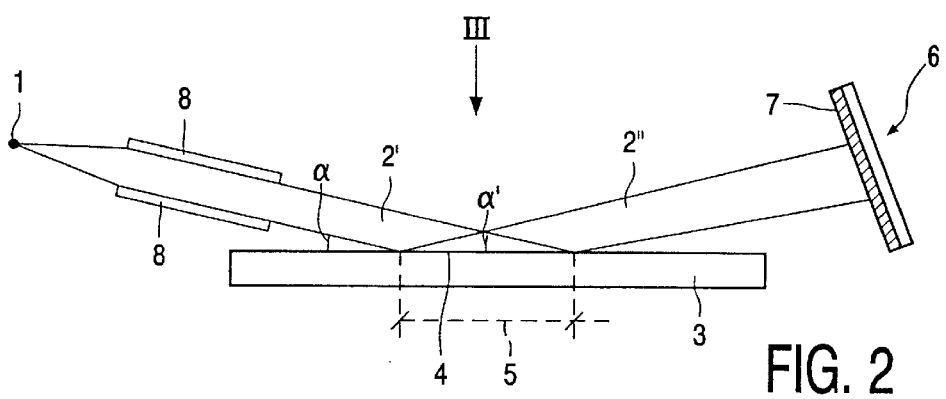
FIG. 2 is a view in conformity with FIG. 1 in the case of parallel radiation.

FIG. 2 shows a corresponding device which, however, operates with parallel radiation instead of diverging radiation. This is achieved by orienting the radiation 2' in parallel between collimating plates 8 that extend in the direction of the plane of drawing. The collimating plates 8 may be arranged, for example at a distance of 10 $\mu$m from one another.

The length of the essentially line-shaped detector in the embodiment shown in FIG. 1 as well as in the embodiment shown in FIG. 2 is such that it extends across the entire area of the reflected radiation 2', so that a measurement can be performed for the entire irradiated area 4 simultaneously. The detector 6, however, may also be smaller and be arranged so as to be displaceable; for the inspection of the entire irradiated area 4 of the sample 3 it is then necessary to perform a plurality of measurements, after a respective shift of the detector 6, in the area of the incident radiation 2'.

Figure 3:
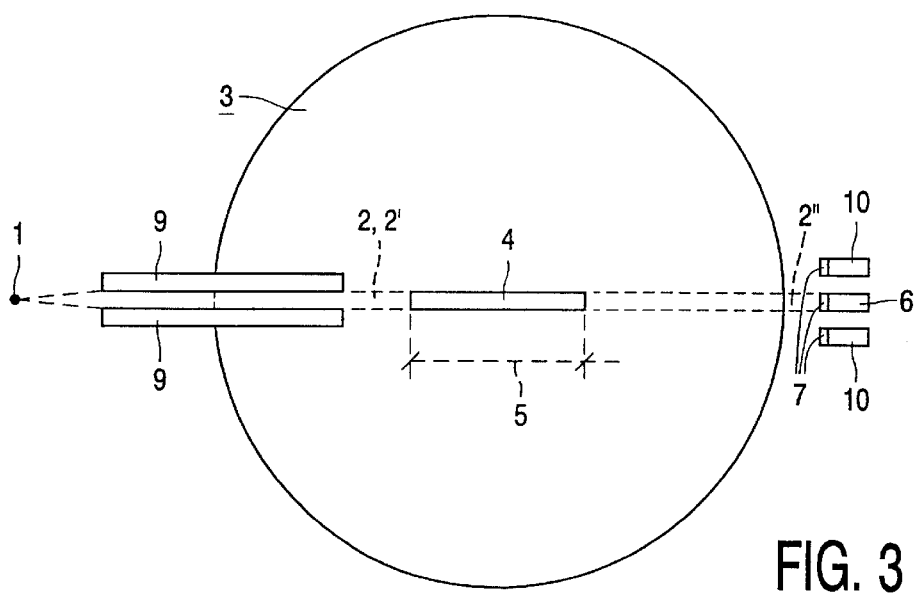
FIG. 3 is a plan view, taken in the direction III, of the arrangement shown in the FIGS. 1 and 2.

FIG. 3 shows that the irradiated area on the surface of the sample 3 is shaped essentially as a line. In the construction shown this is achieved in that the divergence of the radiation 2, 2' is limited in the lateral direction by collimating plates 9. When these plates are situated at a distance of, for example, 200 $\mu$m from one another, the area 4 in FIG. 3 that has a width of approximately 200 $\mu$m and a length 5 of approximately 40 $\mu$m can be irradiated at the same time in dependence on the angle of incidence $\alpha$, $\alpha'$ of the radiation 2, 2' and also in dependence on the distance between the radiation source 1 and the sample 3. FIG. 3 also shows that adjacent the first detector 6, which is arranged in an imaginary plane that extends perpendicularly to the surface of the sample 3 in the direction of the line-shaped radiation area 4, there are arranged two further position-sensitive, energy-sensitive detectors 10 which serve to correct the values measured by the first detector 6 arithmetically in respect of diffuse scattered radiation.

The device in accordance with the invention and the method in accordance with the invention enable a large area of the sample 4 to be inspected simultaneously within a few minutes, that is while utilizing a simple arrangement and without it being necessary to change the position of the radiation source 1 and the sample 3 relative to one another. The inspection of large sample surfaces, therefore, also requires only a very small amount of time when using the method and the device in accordance with the invention, that is, in comparison with conventional methods and devices. The entire sample surface can be inspected by displacing the sample underneath the measuring device and by successively analyzing various areas. Because no focused radiation is used, damaging of the sample by degraded radiation intensity can readily avoided

What is claimed is:

1. A device for inspection of the condition of a sample (3), which device has a stationary radiation source (1) for directing radiation (2, 2'), notably X-rays, onto an area on a surface of the sample (3) to be inspected, and which device also has a position-sensitive, energy-sensitive detector (6) for measuring components (2") of the radiation reflected by the sample (3), characterized in that the radiation source (1) outputs polychromatic radiation and is oriented in such a manner that the radiation (2, 2') is incident on the sample (3) in parallel or diverging rays.

2. A device as claimed in claim 1, characterized in that the angle of incidence ($\alpha$, $\alpha'$) of the radiation (2, 2') on the surface of the sample (3) lies between approximately 0.3° and 1.5°.

3. A device for the inspection of the condition of a sample, notably as claimed in claim 1, which device includes a stationary radiation source (1) wherefrom radiation (2, 2'), notably X-rays, is directed onto an area of the surface of the sample (3) to be inspected, and also includes a position-sensitive detector for measuring components (2") of the radiation that are reflected by the sample (3), characterized in that the radiation source (1) outputs polychromatic radiation and is constructed and oriented in such a manner that the radiation (2, 2') irradiates an essentially line-shaped area (4) on the surface of the sample (3), and that the position-sensitive detector (6) is additionally constructed so as to be energy-sensitive.

4. A device as claimed in claim 3, characterized in that the detector (6) is constructed essentially so as to be line-shaped and is oriented so as to match the line-shaped radiation area (4).

5. A device as claimed in claim 3, characterized in that the radiation (2, 2') that is directed onto the sample (3) is collimated between plates (9) that extend perpendicularly to the plane of the surface of the sample.

6. A device as claimed in claim 5, characterized in that the distance between the plates (9) amounts to approximately 200 $\mu$m.

7. A device as claimed in claim 3, characterized in that at least one further position-sensitive, energy-sensitive detector (10) is arranged adjacent the first detector (6) in order to detect diffuse scattered radiation.

8. A device as claimed in claim 7 characterized in that the detector for the detection of diffuse scattered radiation in provided not only with detector cells that adjoin one another in a linear array, but also with detector cells that adjoin one another in a two-dimensional array.

9. A device as claimed in claim 3, characterized in that the length (5) of the area (4) that is simultaneously irradiated on the surface of the sample (3) amounts to approximately twenty times its width in the direction of the radiation.

10. A method for the inspection of the condition of a sample (3) using a position-sensitive, energy-sensitive detector (6) for measuring a radiation (2, 2') that is emitted by a stationary radiation source (1) and reflected on an area of the sample (3) to be inspected, characterized in the step of orienting the radiation (2, 2') in such manner that it is incident on the sample (3) in parallel or in diverging rays.

11. A method as claimed in claim 10, characterized in that the radiation irradiates an essentially line-shaped area (4) on the surface of the sample (3).

12. A method as claimed in claim 11, characterized in that use is made of an essentially line-shaped detector (6).

13. A method as claimed in claim 12, characterized in that, in addition to the first detector (6), at least one further, position-sensitive, energy-sensitive detector (10) is used to measure diffuse scattered radiation in order to perform an arithmetical correction of the radiation (2") measured by the first detector (6).

14. A method as claimed in claim 11, characterized in that use is made of a two-dimensional detector with primary detector cells that are arranged not only linearly but also of secondary detector cells which are arranged in an adjoining second dimension and via which the diffuse scattered radiation is measured so as to be used for the arithmetical correction of the radiation measured by the primary detector cells.

15. A device for inspection of the condition of a sample, which device has a stationary radiation source (1) for directing radiation (2, 2'), notably X-rays, onto an area on a surface of a sample (3) to be inspected, and which device also has a first position-sensitive, energy-sensitive detector (6) for measuring components (2") of the radiation that are reflected by the sample (3) and a second position-sensitive, energy-sensitive detector (10) arranged adjacent the first position-sensitive, energy-sensitive detector (6) to detect diffuse scattered radiation, characterized in that the radiation source (1) outputs polychromatic radiation and is oriented in such a manner that the radiation (2, 2') is incident on the sample (3) in parallel or diverging rays.

* * * * *